US008124348B2

(12) United States Patent
Zmuda et al.

(10) Patent No.: US 8,124,348 B2
(45) Date of Patent: Feb. 28, 2012

(54) ORAL FLUID RAPID ASSAY FOR HEPATITIS C VIRUS (HCV) ANTIBODIES USING NON-ANTIBODY LABELING OF IGA MOLECULES RECOGNIZING HCV PEPTIDE EPITOPES

(76) Inventors: Jonathan Zmuda, Germantown, MD (US); Lance A. Liotta, Bethesda, MD (US); Gordon Whiteley, Potomac, MD (US)

( * ) Notice: Subject to any disclaimer, the term of this patent is extended or adjusted under 35 U.S.C. 154(b) by 276 days.

(21) Appl. No.: 10/912,405

(22) Filed: Aug. 5, 2004

(65) Prior Publication Data
US 2005/0009011 A1 Jan. 13, 2005

Related U.S. Application Data

(63) Continuation-in-part of application No. 09/938,131, filed on Aug. 23, 2001, now abandoned.

(60) Provisional application No. 60/227,254, filed on Aug. 23, 2000.

(51) Int. Cl.
*G01N 33/576* (2006.01)
*A61K 39/29* (2006.01)
(52) U.S. Cl. ...................... 435/7.1; 424/228.1
(58) Field of Classification Search ............... None
See application file for complete search history.

(56) References Cited

U.S. PATENT DOCUMENTS

| 4,446,232 A | | 5/1984 | Liotta |
| 5,695,930 A | * | 12/1997 | Weinstein et al. ............ 435/5 |
| 5,792,605 A | | 8/1998 | Ochnio et al. |
| 5,942,407 A | * | 8/1999 | Liotta et al. .................... 435/28 |
| 5,965,390 A | * | 10/1999 | Bjorck et al. ................. 435/69.1 |
| 6,054,264 A | * | 4/2000 | Chien et al. ...................... 435/5 |

OTHER PUBLICATIONS

McIntyre et al. Eur. J. Microbiol. Infect. Dis. 1996, vol. 15, p. 882-884.*
Sato et al. (Digestive Diseases and Sciences, 1994, vol. 39, p. 2022-2031).*
Bello et al. (European Journal of Clinical Microbiology and Infectious Diseases, 1998, vol. 17, p. 570-572).*
Elsana, S. et al., "HCV antibodies in saliva and urine." J. Med. Virol., vol. 55, 1998, pp. 24-27, XP002215072.
Taliani, G. et al., "Hepatitus C virus infection of salivary gland epithelial cells." J. Hepatol., vol. 26, 1997, pp. 1200-1206, XP002215073.
Van Doornum, G.J.J. et al., "Evaluation of hepatitis C antibody testing in saliva specimens collected by two difference systems in comparison with HCV antibody and HCV RNA in serum." J. Med. Virol., vol. 64, 2001, pp. 13-20, XP002215074.

* cited by examiner

*Primary Examiner* — Bao Li
(74) *Attorney, Agent, or Firm* — Fay Sharpe LLP (57) ABSTRACT

A method and device to detect Hepatitis C (HCV) antibodies in oral fluid is provided. This method introduces a non-antibody detection molecule that labels all classes of patient antibodies in oral fluid, followed by the specific concentration of labeled anti-HCV antibodies by selective capture in a trapping zone consisting of peptide antigens derived from the HCV genome. Signal generated by the labeled antibodies present in the trapping zone is proportional to the number of anti-HCV antibodies bound to the antigens present in the trapping zone. Presence of signal derived from the capture of antibody/detection molecule complexes in the trapping zone is indicative of past exposure to HCV.

10 Claims, 7 Drawing Sheets

ORAL FLUID RAPID ASSAY FOR HEPATITIS C VIRUS (HCV) ANTIBODIES USING NON-ANTIBODY LABELING OF IGA MOLECULES RECOGNIZING HCV PEPTIDE EPITOPES

The present application is a continuation-in-part of U.S. Application Ser. No. 09/938,131 filed on Aug. 23, 2001, now abandoned, which claims the benefit of the filing date of U.S. Provisional Application Ser. No. 60/227,254, filed Aug. 23, 2000.

FIELD OF THE INVENTION

The ability to detect anti-HCV in oral fluid is useful for the rapid detection of HCV exposure by non-invasive means. The methods provided in the invention are also useful in the early detection of HCV infection by recognition of anti-HCV of the IgA class, monitoring of antiviral therapy, genotyping of HCV virus, determining immune response to individual HCV epitopes, and monitoring potential vaccination programs.

BACKGROUND OF THE INVENTION

Hepatitis C (HCV) is the major cause of parenterally transmitted non-A, non-B hepatitis (Choo et al., 1989 Science 244:359-362; Kuo et al., 1989, Science 244:362-364) with a prevalence of 1-3% throughout the world (Davis et al., 1998, Hepatology 28 (Suppl 4, pt 2):99A). Chronic disease develops in 60-85% of patients, with cirrhosis representing a major hallmark of HCV infection. Among patients whose infection progresses to cirrhosis, as many as 1-4% develop hepatocellular carcinomas annually (Fattovich et al., 1997, Gastroenterology 112:463-472). It is estimated that the need for hepatic transplantation for infected individuals will increase 5-7 fold in the next 20 years unless more effective treatments and preventative programs are introduced (Davis et al., 1998, Hepatology 28 (Suppl 4, pt 2):99A).

While additional anti-viral therapies are needed to combat the spread of HCV, equally necessary is the development of a rapid, highly sensitive and cost-effective test to detect and monitor HCV within the population. Current PCR and ELISA-based assays for the detection of HCV are costly, relatively slow and reliant upon serum or plasma as the sample fluid. The substitution of oral fluid for serum in HCV assays would provide a cost-effective, non-invasive means to conduct routine screening and would facilitate sample procurement from patient groups where serum collection is difficult, such as intravenous drug users, who constitute a significant portion of total HCV cases.

A number of oral fluid-based assays have been designed for the detection of viral antibodies with good results. Virus-specific antibodies have been detected in the oral fluid of patients infected with human immunodeficiency virus (Major et al., 1991, J. Infect. Dis. 163:699-702), hepatitis A (Stuart et al., 1992, Epdiem. Infect. 109:161-166), hepatitis B (Ben Aryeh et al., 1985, Arch. Oral Biol. 30:97-99), rubella (Saleh, 1991, J. Egypt Public Health Assoc. 66:123-124,) and following immunization against polio (Zaman et al., 1991, Acta Paediatrica Scan. 80: 1166-1173), rotavirus (Ward et al., 1992, J. Med. Virol. 36: 222-225) and hepatitis A (Laufer et al., 1995, Clin. Infect. Dis. 20:868-871). For HCV, ELISA-based assays developed initially for use with serum or plasma have been modified to detect anti-HCV antibodies in oral fluid (Cameron et al., 1999, J. Viral Hepatitis 6:141-144; Elsana et al., 1998, J. Med. Virol 55:24-27; McIntyre et al., 1996, Eur. J. Clin. Microbiol. Infect. Dis. 15:882-884; Sherman et al., 1994, Amer. J. Gastroent 89:2025-2027; Thieme et al., 1992, J. Clin. Microbiol. 30:1076-1079); using a modified protocol with the HCV 3.0 ELISA (Ortho Diagnostic Systems), (McIntyre et al. 1996, Eur. J. Clin. Microbiol. Infect. Dis. 15:882-884) detected anti-HCV antibodies within a group of 18 HCV(+) and 49 HCV(−) oral fluid samples with 72% sensitivity and 98% specificity. In the same study, 100% sensitivity and 100% specificity was achieved using the Monolisa HCV assay (Sanofi Pasteur Diagnostics, France). It is unclear what the differences were that lead to the increased sensitivity of the Monolisa test, and thus care must be taken in the interpretation of results obtained from tests not designed specifically for use with oral fluid. None of these assays has achieved the sensitivity required for a rapid point of care test. None of these assays has disclosed the special role of oral fluid IgA in human oral fluid as a key determinant of sensitivity and specificity for HCV screening.

An intrinsic difficulty in designing oral fluid-based diagnostic assays, however, is detecting a sufficient proportion of the relatively low levels of antibody present in oral fluid to generate a meaningful diagnostic result. Indeed, it is estimated that overall antibody levels are 800-1000-fold lower in oral fluid than in serum (Parry et al., 1987, Lancet 2:72-75) making detection sensitivity of the utmost importance in oral fluid-based tests. While this problem is significant, an HCV assay designed to be used specifically with oral fluid as the diagnostic fluid, and not simply a serum-based assay modified for use with saliva, could overcome this complication and provide an important test for HCV in the population.

SUMMARY OF THE INVENTION

The invention disclosed is a means to detect antibodies against HCV using oral fluid as a sample medium. Assays in the prior art have not achieved the sensitivity and specificity required to rapidly screen HCV infection in human oral fluid. Most critically, the use of a labeled detection molecule that recognizes not only IgG, but all classes of immunoglobulins, enhances the ability to detect anti-HCV in oral fluid in an ELISA format or using a flow-through system. When detecting anti-HCV using a labeled detection molecule that recognizes only anti-HCV of the IgG class, detection sensitivity was vastly reduced. The incorporation of a detection method that labels multiple classes of anti-HCV, on the other hand, allows for increased detection sensitivity of samples that would otherwise be scored negative using a detection method that only recognizes IgG.

By coupling this detection method to an assay that utilizes a membrane with immobilized HCV peptide antigens present as a trapping zone, followed by subsequent flow of sample through the trapping zones and selective binding of labeled antibodies specific for HCV epitopes within the trapping zone, an immunoassay for the detection of anti-HCV can be performed in a short time period (<15 minutes). The ability to use oral fluid as a sample is of great value to such a rapid diagnostic tool since oral fluid can be collected rapidly and used immediately following collection. An assay using oral fluid, performed on a miniature test platform, analyzed in a small light gathering machine, and able to be completed within 15 minutes from start to finish would be of enormous value as a screening agent for HCV in the population. By decreasing the time of the assay and eliminating the need for invasive blood-based sample acquisition, such an assay would certainly increase the ability to screen, detect and monitor HCV within the population.

The use of an assay to detect anti-HCV in saliva would also be of benefit in the rapid and non-invasive detection of antibodies following vaccinations and monitoring of vaccination efficacy over time, monitoring therapeutic response of patients to treatment regimes and screening for early infection, as IgA antibodies are known to be an important part of the early stages of the immune response.

Thus, the present invention seeks to overcome the deficiencies of the prior technology by designing an HCV assay that would meet the following objectives. A first objective is that the test is non-invasive, generates minimal risk of infection to those administering the test and can be performed from start to finish by non-medical personnel.

A second objective is that the test is rapid (<15 min.).

A third objective is that the test is specialized to detect the specific class of anti-HCV antibodies in oral fluid, and is not simply a modification of a current serum-based assay.

A fourth objective is that the test incorporates a number of different HCV antigens to minimize false negative results.

A fifth objective is that the test is adaptable to future incarnations of the assay to meet specific diagnostic needs, and that it is sensitive enough to detect extremely low levels of anti-HCV.

BRIEF DESCRIPTION OF THE DRAWINGS

FIG. 2: Components of the HCV strip immunoassay. (A) Top view of disassembled assay cassette showing the position of the nitrocellulose test strip as well as the top and bottom wicks and the substrate-coated gelbond. The "trapping zone" is located directly beneath the substrate-coated gelbond. The trapping zone and substrate-coated gelbond are kept from contacting one another until such time as the cassette is inserted into the luminometer for reading. (B) Top view of an assembled cassette with the conjugate hinge in the open position. (C) Top view of an assembled cassette with the conjugate hinge in the closed position. Also visible in C is the chase injection port and the luminescence measuring window. (D) Side view of assembled cassette showing the conjugate hinge in the open position as well as the lever on the back of the cassette that is contacted by the Junior luminometer upon insertion to bring the anti-HCV/anti-human-AP complex captured in the trapping zone into contact with the substrate-coated gelbond suspended above and thus initiate the luminescence reaction.

DETAILED DESCRIPTION OF THE INVENTION

Figure 7:
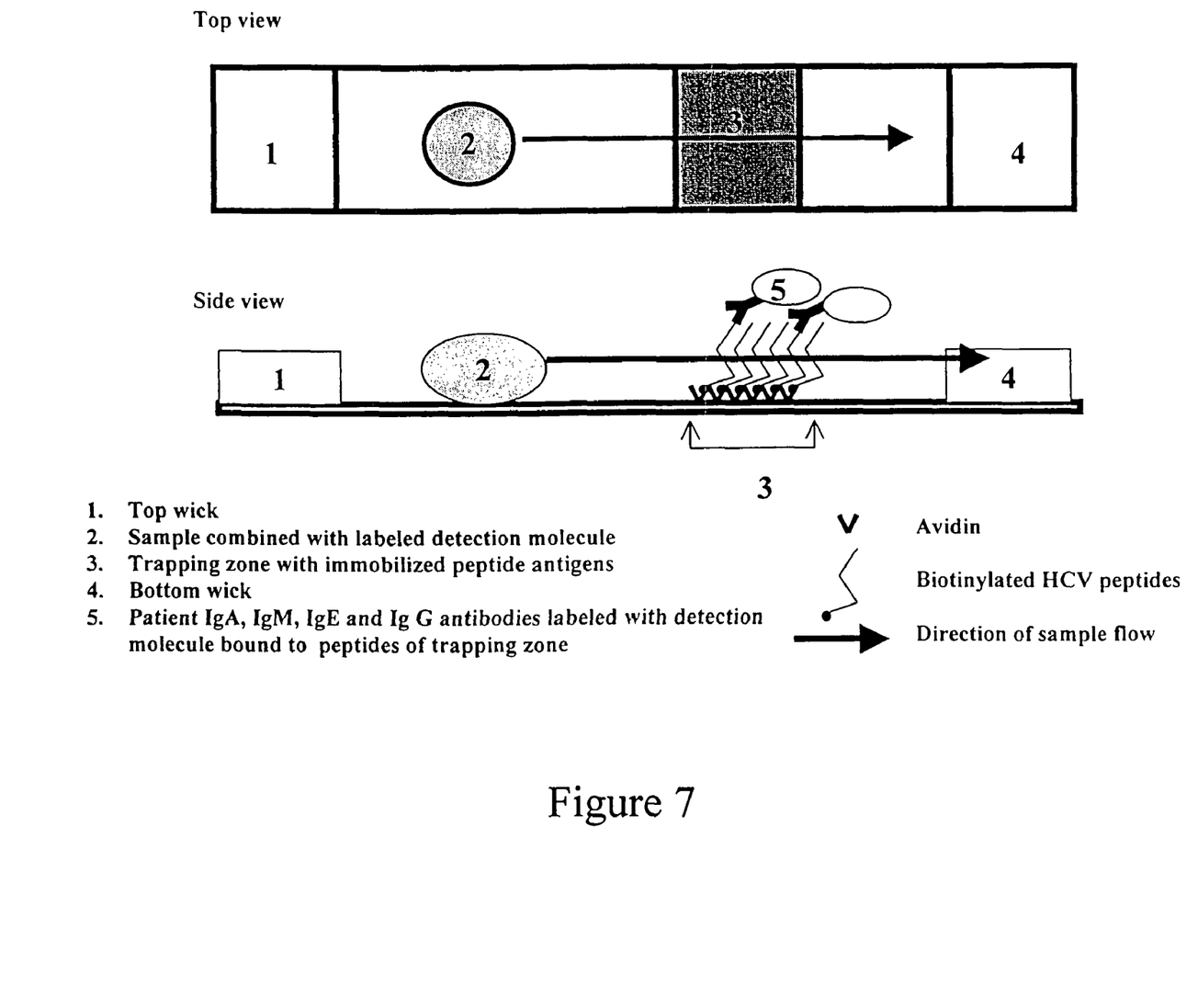
FIG. 7 Diagram of the steps of the process according to one embodiment of the invention.

The invention described herein represents the ability to detect HCV exposure in oral fluid by labeling and detecting multiple classes of anti-HCV instead of anti-HCV IgG alone. Saliva is first collected by a device independent of the test module. A volume of crude saliva is then added to the test module wherein it mixes with a detection molecule that labels all classes of human antibodies. The antibody-detection molecule complex then passes through a trapping zone comprised of immobilized HCV peptide antigens. Antibody/detection molecule complexes that are recognize the HCV sequences represented in trapping zone bind and are thus immobilized within the zone (FIG. 7). The addition of a suitable substrate for the detection molecule allows for generation of a signal in samples possessing antibodies to HCV and thus correlates with HCV exposure. In a particular embodiment the non-antibody label protein is protein LA conjugated to an enzyme which generates a chemiluminescent signal that is read in a luminometer.

EXAMPLES

I. Detection of Multiple Classes of Anti-HCV in Oral Fluid to Increase Detection Sensitivity.

The detection of multiple classes of anti-HCV in oral fluid can increase the H detection sensitivity of the Ortho HCV 3.0 ELISA to levels comparable with those attained using serum samples. Patients for this study were pre-selected from one of eleven participating clinical sites and shown to be either HCV positive or negative based on a clinical diagnosis according to the CDC testing algorithm (Alter et al., 1998). Serum samples were further confirmed by repeat in-house testing using the Ortho HCV 3.0 ELISA following the manufacturer's instructions. Oral fluid samples were collected using a Salivette (Sarstedt Research, Germany) whereby a polyester-coated cotton plug is placed in the mouth of the patient until saturation and is then centrifuged in a carrier tube for 5 minutes to extract the oral fluid. The Salivette was chosen for its ease of use and because it does not use a sample buffer to dilute the specimens. Paired samples were shipped overnight at 4° C.

and processed immediately upon arrival. Samples were then stored at −80° C. until testing.

Figure 1:
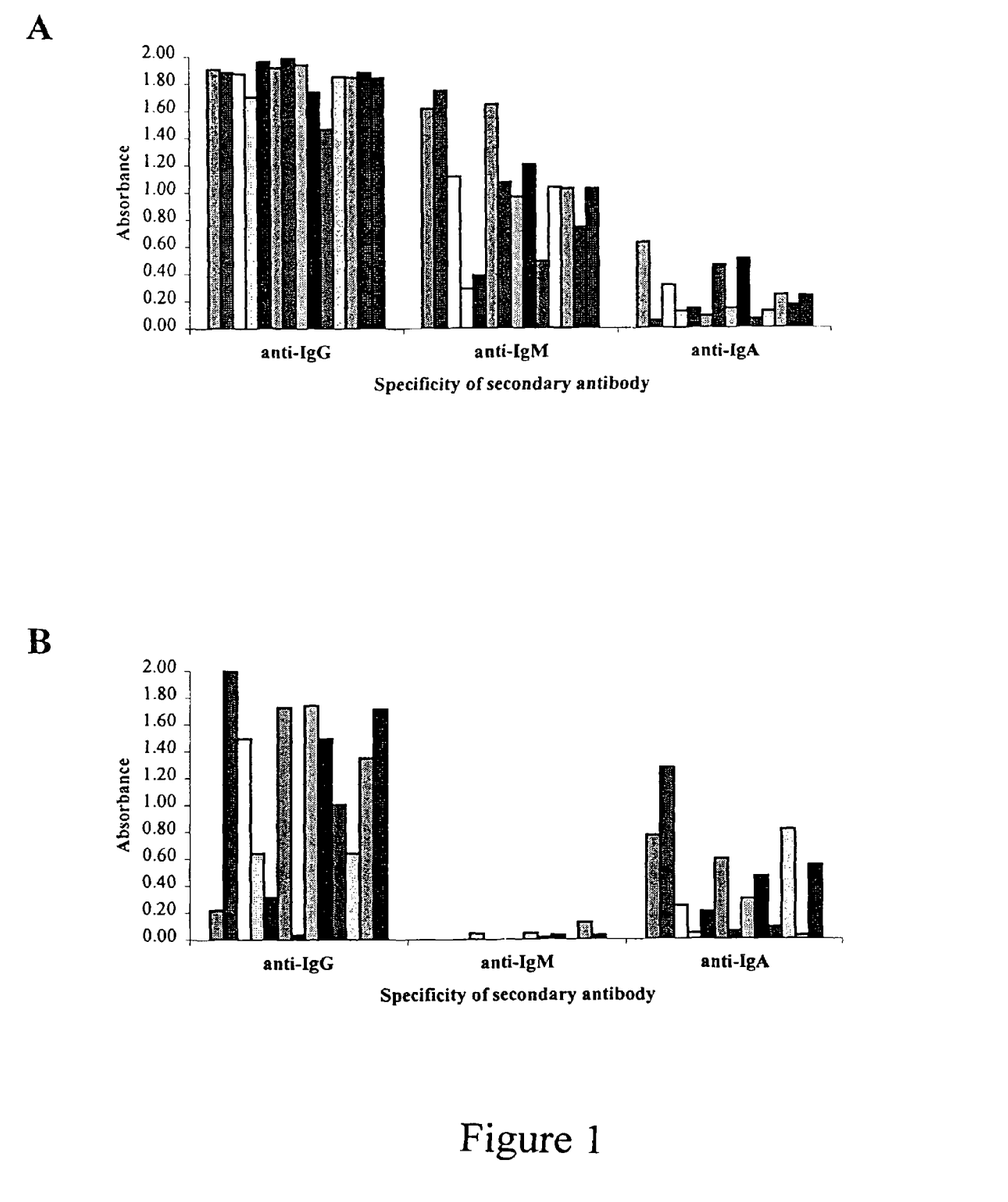
FIG. 1. Characterization of multiple classes of anti-HCV present in serum and oral fluid. Paired serum/oral fluid samples were screened by HCV 3.0 ELISA using enzyme-conjugated antibodies specific for human IgG, IgM or IgA, respectively. (A) In serum, high levels of anti-HCV IgG and IgM class antibodies are detectable, while relatively little anti-HCV IgA is present. (B) In oral fluid, the majority of antibodies detectable are of the IgG or IgA class with little or no anti-HCV IgM present.

To determine if specific classes of antibodies were preferentially enriched in serum or oral fluid samples, the composition of anti-HCV present in both fluids was examined. Fourteen paired HCV-positive oral fluid/serum samples (with sufficient volumes of oral fluid for multiple ELISA assays) were chosen for ELISA analysis and examined using secondary enzyme-conjugated antibodies (Jackson Immunoresearch) that recognize only IgG, IgM or IgA, respectively, to identify the different classes of anti-HCV detectable in oral fluid (FIG. 1). Modification of the HCV 3.0 was necessary to achieve optimal detection sensitivity and specificity; compared to the manufacturer's instructions for use with serum, oral fluid sample volume was increased from 10 μl to 100 μl per well and sample incubation time was increased from 1 hour at 37° C. to overnight at 4° C. Furthermore, a more sensitive two-part TMB substrate kit (Pierce) was used for all testing in place of the o-phenylenediamine tablets supplied with the HCV 3.0 kit. Analysis of the optical densities (OD) generated by these 14 samples showed that anti-HCV of the IgG and IgM class was most abundant in serum samples (mean OD=1.85, 1.03, respectively), with little IgA class anti-HCV present (OD=0.24; FIG. 1A). These samples were not treated for rheumatoid factor, however, and thus it is possible that elevated levels of anti-IgM reactivity in serum samples may be attributable to the presence of this interfering substance (see Genser et al., 2001). In contrast, while IgG (OD=1.10) remained the major class of anti-HCV detectable in oral fluid samples using the HCV 3.0 assay, a higher level of anti-HCV IgA (OD=0.42) was also detectable, while nearly no anti-HCV IgM was present (OD=0.02; FIG. 1B). Statistically, the mean OD of anti-HCV of the IgG and IgM class is significantly reduced in oral fluid compared to serum ($P<0.01$), while the OD of IgA class anti-HCV is not significantly different ($P>0.01$).

Unexpectedly, in a number of oral fluid samples possessing low anti-HCV IgG levels, a significant amount of anti-HCV IgA was detectable (FIG. 1B) which might contribute to a higher overall OD and thus render a positive result. Indeed, the ability to detect anti-HCV of the IgA class may also increase the likelihood of detection early on during the course of infection, as IgA is known to be present during the earliest stages of the immune responses to infections. (Freihorst and Ogra, 2001).

An investigation was then conducted to determine whether the detection of multiple classes of anti-HCV antibodies, instead of IgG alone, could increase the sensitivity of the Ortho HCV 3.0 ELISA in a modified oral fluid-based format. Paired oral fluid/serum samples from 127 known HCV seropositive and 31 seronegative donors were screened using the HCV 3.0 assay according to the manufacturer's instructions using the monoclonal anti-human IgG-peroxidase detection antibody. Using serum samples, 100% sensitivity and specificity with the HCV 3.0 assay was achieved (Table I).

TABLE I

Sensitivity and specificity of HCV 3.0 assay using paired serum/oral fluid samples with different enzyme-conjugated secondary antibodies.

| | Serum | | | Serum | |
|---|---|---|---|---|---|
| Oral fluid | Positive | Negative | Oral fluid | Positive | Negative |
| Positive | 103 | 0 | Positive | 127 | 0 |
| Negative | 24 | 31 | Negative | 0 | 31 |

TABLE I-continued

Sensitivity and specificity of HCV 3.0 assay using paired serum/oral fluid samples with different enzyme-conjugated secondary antibodies.

| Conjugate: | Monoclonal anti-human IgG | Goat anti-human IgG + IgM + IgA |
|---|---|---|
| Sensitivity: | 81% | 100% |
| Specificity: | 100% | 100% |

Because there is no accepted cutoff value for oral fluid in the HCV 3.0 kit, sensitivity and specificity were determined by ROC analysis at the 95% confidence interval as well as by determining a cutoff 3.5SD above the mean of the 31 HCV negative samples. Using the modified incubation protocol mentioned previously, along with the anti-IgG conjugate antibody of the HCV 3.0 kit, detection sensitivity was reduced to 81% (103/127) while specificity remained 100%.

Oral fluid samples were then re-screened using a 1:16,000 dilution of peroxidase-labeled goat anti-human IgG+IgM+IgA antibody cocktail (Kirkgaard and Perry Laboratories, Gaithersburg, Md.) in PBS/1% BSA/10% goat serum instead of the monoclonal anti-human IgG provided with the HCV 3.0 kit. This antibody dilution proved to have the greatest signal:noise ratio in titration studies and was used in all studies in which the antibody cocktail was included. Using this modified protocol, anti-HCV was detected in patient oral fluid samples with 100% sensitivity and specificity by ROC analysis or using the calculated 3.5SD cutoff (cutoff=0.026; Table I). All oral fluid samples from HCV positive individuals that were initially scored negative using the Ortho HCV 3.0 anti-IgG conjugate were subsequently scored positive when detected using the anti-IgG+IgM+IgA cocktail (Table II).

TABLE II

Discrepant analysis of select patient oral fluid samples possessing low anti-HCV IgG.

| | Oral fluid | | Serum |
|---|---|---|---|
| | Conjugate | | |
| Patient # | (anti-IgG) | (anti-IgG + M + A) | (anti-IgG) |
| 103-19 | 0.014 | >3.5 | 2.42 |
| 109-03 | 0.014 | 2.24 | 2.25 |
| 103-15 | 0.149 | 2.60 | 2.07 |
| 109-01 | 0.213 | 2.77 | 2.33 |
| 103-01 | 0.293 | >3.5 | 2.34 |
| 103-37 | 0.357 | 2.29 | 1.56 |
| 108-06 | 0.378 | >3.5 | 2.40 |

The results indicate that the use of a secondary antibody cocktail that recognizes not only IgG, but IgA and IgM as well, may aid in the detection of the relatively low levels of anti-HCV antibodies present within oral fluid and thus increase detection sensitivity. This increase in detection sensitivity when such an antibody cocktail is used is in good agreement with data showing that a significant percentage of anti-HCV antibodies in oral fluid exist in the form of IgA class antibody molecules (see FIG. 1). A recent study by Van Doornum et al. (2001) showed that anti-HCV could be detected with up to 88% sensitivity in oral fluid using a modified protocol with the Mono-Lisa anti-HCV Plus kit. Similar to the Ortho HCV 3.0 assay, however, this kit utilizes an anti-human IgG conjugate antibody, and is therefore incapable of detecting IgA class anti-HCV present in oral fluid samples. Furthermore, in contrast to the HCV 3.0 assay, the Mono-Lisa does not incorporate proteins from the core region of the HCV proteome and sensitivity in oral fluid may be reduced by the inability to capture antibodies directed against this highly antigenic region. By detecting multiple classes of antibodies, and through the use of an ELISA with a high percentage of the total antigenic sequences of HCV coated onto the solid phase, an increase in detection sensitivity to levels comparable to those obtained from serum-based analysis was achieved.

Thus, the results of this study show that detection of anti-HCV IgG, IgM and IgA in oral fluid samples is essential for correctly diagnosing patient samples possessing relatively low levels of anti-HCV IgG. Indeed, patient oral fluid samples with low anti-HCV IgG levels will escape detection in immunoassays that recognize only IgG class immunoglobulins. By effectively increasing the pool of antibodies detectable in oral fluid samples it is possible to overcome the intrinsic difficulty of detecting the extremely low levels of antibodies in oral fluid and allow for the generation of novel non-blood based immunoassays.

Figure 2:
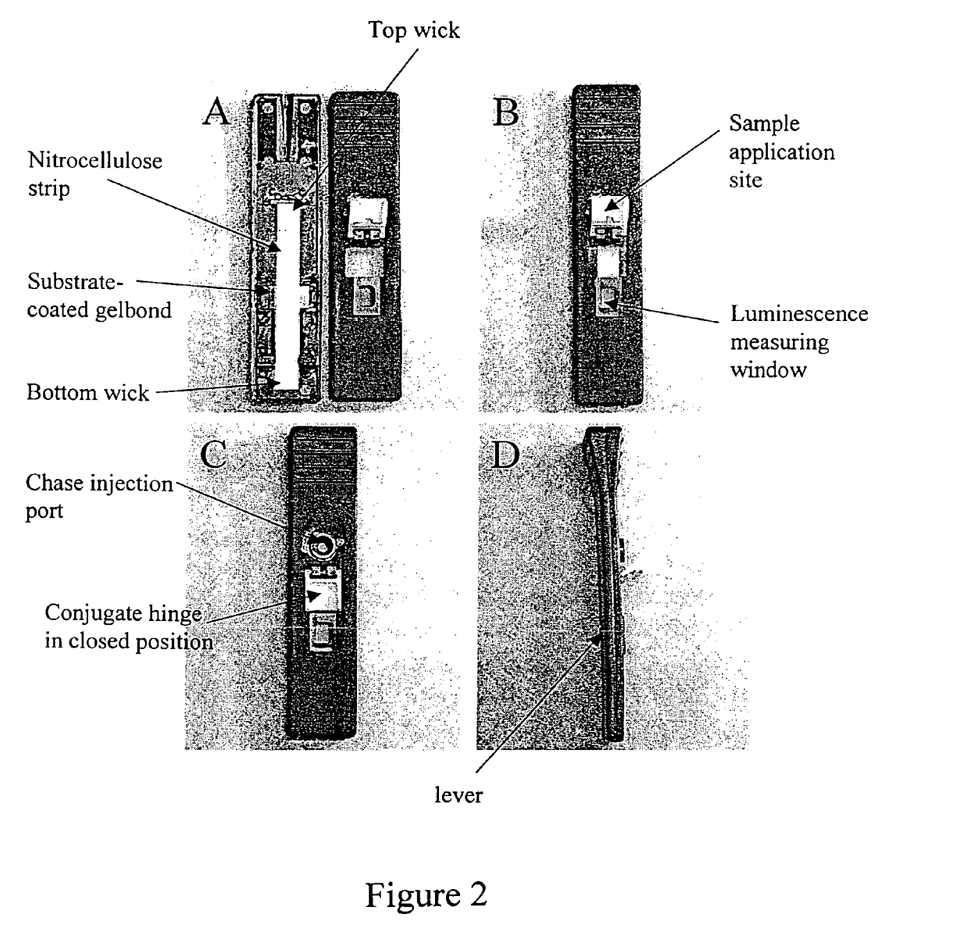

II. Components of the Test Module for the Oral Fluid Based Lateral Flow Immunoassay The HCV immunoassay consists of a single nitrocellulose strip with a mixture of recombinant HCV antigens immobilized in a trapping zone 2.4 cm from the top edge of the strip. The nitrocellulose strip is held stationary within a custom-made plastic cassette assembly (FIG. 2A). Oral fluid sample and AP-conjugated goat anti-human IgG+IgM+IgA antibody cocktail are added to the conjugate hinge (FIG. 2B) creating a complex of anti-HCV bound by anti-human-AP antibodies. Alternatively, Protein LA conjugated to alkaline phosphatase can be used as the detection molecule. The hinge is then closed and pressed onto the nitrocellulose test strip for 5 seconds. 60 µl of chase solution is then added to a port on the top of the cassette located just above the hinge region (FIG. 2C) facilitating the migration of sample complex down the nitrocellulose test strip toward the trapping zone while simultaneously washing unbound conjugate antibody through the trapping zone to the bottom wick to prevent non-specific enzyme luminescence within the trapping zone. Upon reaching the trapping zone, the anti-HCV antibody present in the anti-HCV/anti-human-AP complex binds its cognate antigen, thus ceasing its migration. Dried AP substrate is suspended above the trapping zone (FIG. 2A) on a piece of gelbond preventing the substrate from coming into contact with the anti-HCV/anti-human-AP complex in the trapping zone until the cassette is inserted into the luminometer. Four minutes after the addition of the chase solution, the test cassette is inserted into the luminometer. A lever on the back of the cassette is depressed by the luminometer (FIG. 2D) bringing the substrate into contact with the anti-HCV/anti-human-AP complex in the trapping zone, thus initiating the luminescence-generating reaction. Luminescence is measured through the window in the top of the cassette for 1 minute.

III. Selection of HCV Peptide Sequences to be Incorporated into Trapping Zone of Rapid Immunoassay Peptide sequences shown to be strongly antigenic were chosen for synthesis and screening for incorporation into the trapping zone of the HCV immunoassay. U.S. Pat. No. 5,698,390 describes the sequencing of the HCV genome and the use of specific, highly antigenic sequences as tools for immunoassay development of blood-based HCV assays. These sequences, however, have not yet been useful in the detection of HCV in oral fluid with high degrees of sensitivity and specificity for use in screening. Contrary to other assays for HCV exposure, peptides were chosen based on these sequences instead of recombinant antigens for a number of reasons: firstly, since the nucleotide sequence of HCV is well known and many of the strongly antigenic epitopes mapped in detail, highly purified peptides that represent only the strongly antigenic regions of the HCV genome can be synthesized rapidly and in large quantity at relatively low cost. Secondly, because new peptide antigens incorporating different antigenic sequences can be synthesized rapidly, new antigens can be added, or substituted, for peptides already in the assay with relative ease. Thirdly, by incorporating only the highly antigenic sequences of the HCV genome, thus eliminating all non-antigenic sequences, the specificity of the assay can be improved.

On the basis of data generated by screening 30 patient serum samples against individual peptide antigens in an ELISA format, five HCV sequences were chosen. All 30 serum samples were reactive against at least one of the five peptide antigens (Table III). The following sequences represent the amino acids numbers based on Kato et al. (1990) chosen for use: 7-26, 22-41, 1694-1710, 1710-1728 and 1924-1943. These sequences represent two peptides from the core region of the HCV genome and three peptides from the NS4 region, respectively.

TABLE III

Selection of peptides for use in the trapping zone. Thirty serum samples were screened against individual peptides by ELISA. All 30 samples showed reactivity against at least one of the 5 peptides tested.

| | Peptide antigen (aa #s) | | | | |
|---|---|---|---|---|---|
| | 7-26 | 22-41 | 1694-1710 | 1710-1728 | 1924-1943 |
| Sensitivity (%) | 97 | 97 | 86 | 90 | 83 |

Figure 3:
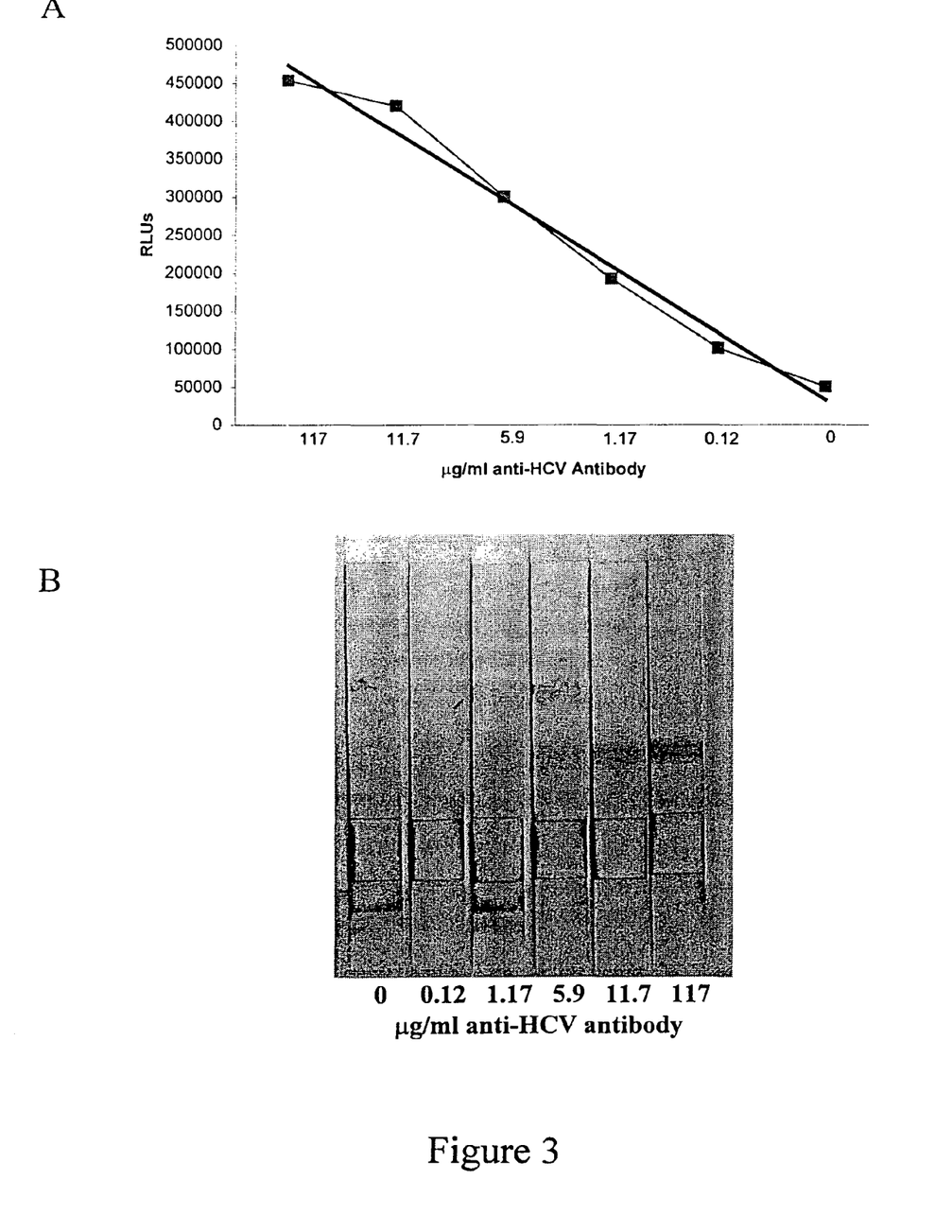
FIG. 3: Dose response curve for spiked monoclonal anti-HCV antibodies in an HCV(−) oral fluid sample. Monoclonal anti-HCV antibodies were spiked into an HCV(−) oral fluid sample to test the ability of the mixed antigen trap to capture anti-HCV antibodies. (A) Dose response curve for spiked monoclonal anti-HCV antibodies present in oral fluid at concentrations ranging from 0-117 μg/ml. (B) Digital photograph of nitrocellulose test strips post-stained with NBT/BCIPT corresponding to the data points in (A). Staining within coherent trapping zones is visible in all spiked samples while no staining is present in the non-spiked control.

IV. Rapid Screening of Oral Fluid Samples for Anti-HCV Using an Affinity Trap Immunoassay Detection of Monoclonal Anti-HCV Antibodies Spiked into Oral Fluid To determine if low levels of monoclonal anti-HCV antibodies in oral fluid are detectable by the HCV LNSI, a mixture of antibodies against the core, NS3, NS4 and NS5 antigens was added to an HCV(−) oral fluid sample for a final concentration of antibody ranging from 0 to 117 µg/ml. Since all monoclonals were of the IgG subtype, an AP-conjugated goat anti-mouse IgG secondary antibody was used to form the anti-HCV/anti-mouse-AP complex. RLUs for the most concentrated spiked sample were 9-fold higher than those obtained for the 0 µg/ml sample (453584 vs. 50568). From the values obtained a dose response curve was generated with an $R^2=0.98$ (FIG. 3A).

To observe the binding of the anti-HCV/anti-mouse-AP complex within the trapping zone visually, cassettes were disassembled following luminescence measurement and the nitrocellulose strips were then stained for 7 min. with NBT/BCIP AP substrate. A coherent trapping zone is visible for assays employing 1.17 to 117 µg/ml spiked monoclonal antibodies in oral fluid (FIG. 3B). At 0.12 µg/ml a faint band within the trapping zone is present, while at 0 µg/ml no band is visible within the trapping zone.

Detection of Anti-HCV in Oral Fluid Samples

Sixty-four known HCV(+) oral fluid samples and 14 known HCV(−) samples were screened using the invention. A cutoff value was assigned by taking the mean values of the 14 HCV(−) samples plus 2 standard deviations. Using this cutoff value, 63/64 of the known patient samples were scored positive (FIG. 4) leading to a calculated sensitivity of 98.4%.

None of the HCV(−) samples obtained values greater than that of the calculated cutoff for a specificity of 100%.

Figure 4:
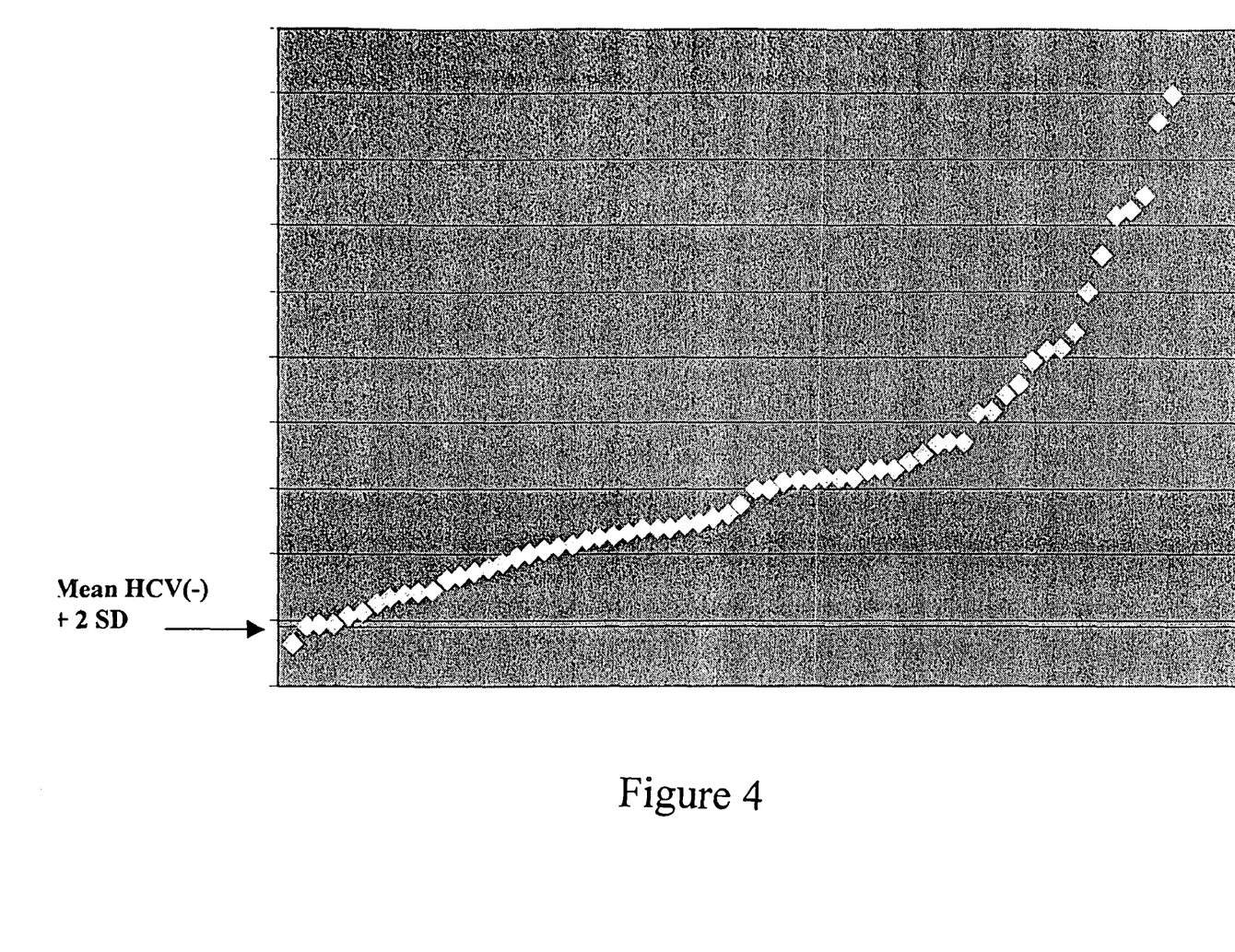
FIG. 4. Screening of 64 known HCV(+) saliva samples on strip immunoassay. A cutoff was determined using the mean of 14 HCV(−) saliva samples+2SD. 63/64 known HCV(+) saliva samples generated values above the calculated cutoff for a sensitivity of 98.4%.

To visualize the luminescence reaction directly, HCV(+), and HCV(−) saliva samples were imaged by a CCD Light Imager. Assays were conducted in the same manner as described previously with the exception that sticks were imaged in the NightOwl (Bertold Inc. Germany) to detect total luminescence. While HCV (+) samples possess high levels of luminescence, nearly no luminescence is detectable in the HCV(−) sample (FIG. 4).

V. V. Serial Trapping Zones to Type Antibodies Against Specific Peptides of the HCV Virus.

Six HCV peptide antigens were coated as individual trapping zones onto a nitrocellulose matrix to demonstrate the ability of the invention to differentially display the patient antibody response from individual subjects. Samples were mixed with Protein LA conjugated to alkaline phosphatase and allowed to migrate through the 6 different trapping zones. During this migration, patient antibodies to the different antigens were selectively captured in the individual trapping zones allowing for a more detailed analysis of the patient antibody response. The peptide composition of each trapping zone was as follows: line 1 aa 384-403, line 2 aa 7-26, line 3 aa 22-41, line 4 aa 1694-1710, line 5 aa 1710-1728, line 6 aa 1924-1943.

Figure 5:
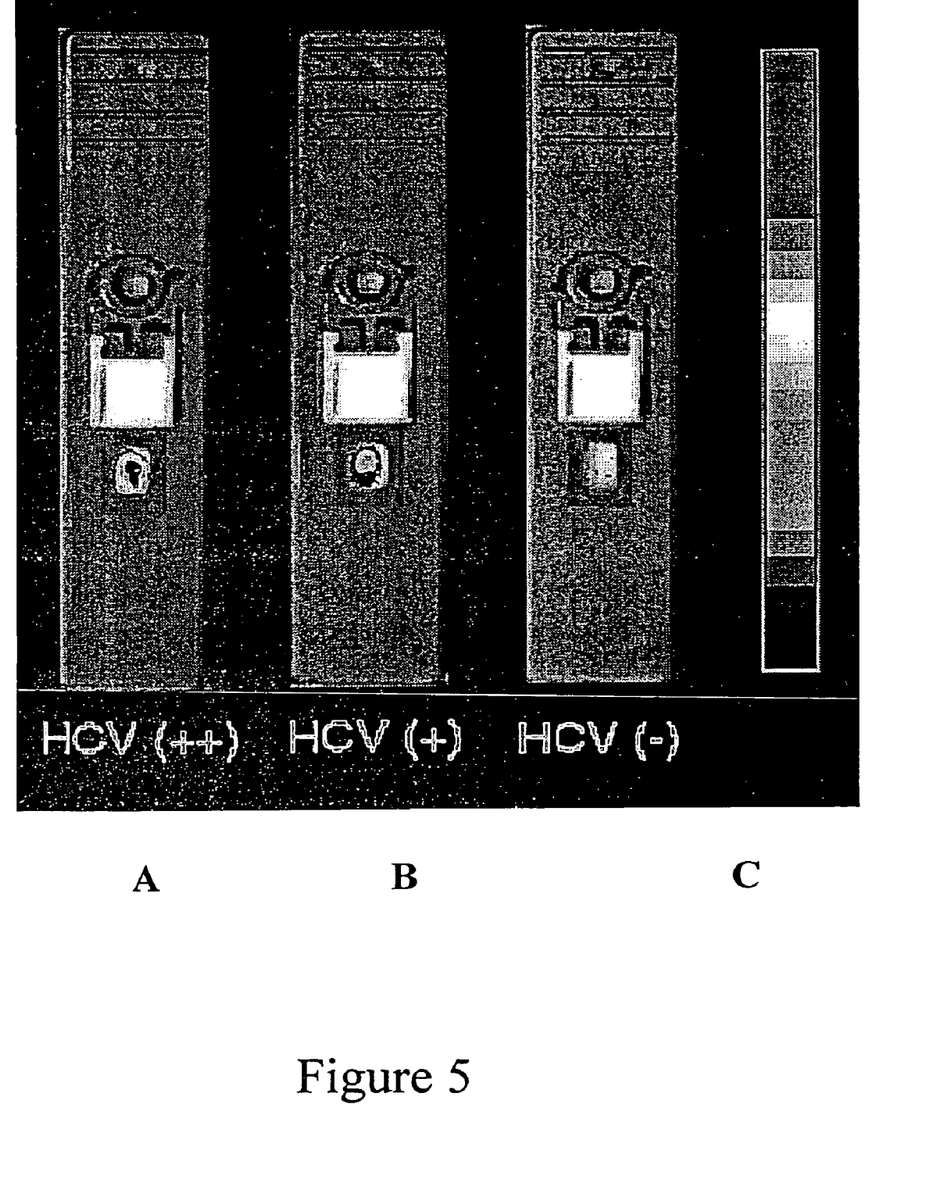
FIG. 5: Direct visualization of HCV LNSI assays using the NightOwl Molecular Light Imager. To observe the relative amounts of luminescence produced by highly immunoreactive oral fluid samples (HCV(++)), weakly reactive samples (HCV(+)) and HCV(−) samples, luminescence was collected (60 sec exposure time) by the NightOwl Molecular Light Imager. A luminescence intensity scale is provided for reference with purple representing the most intense regions of luminescence. (A) A highly immunoreactive oral fluid sample generated extensive luminescence within the collection window just below the closed conjugate hinge assembly. (B) A weakly immunoreactive oral fluid sample. (C) An HCV (−) oral fluid sample.
Figure 6:
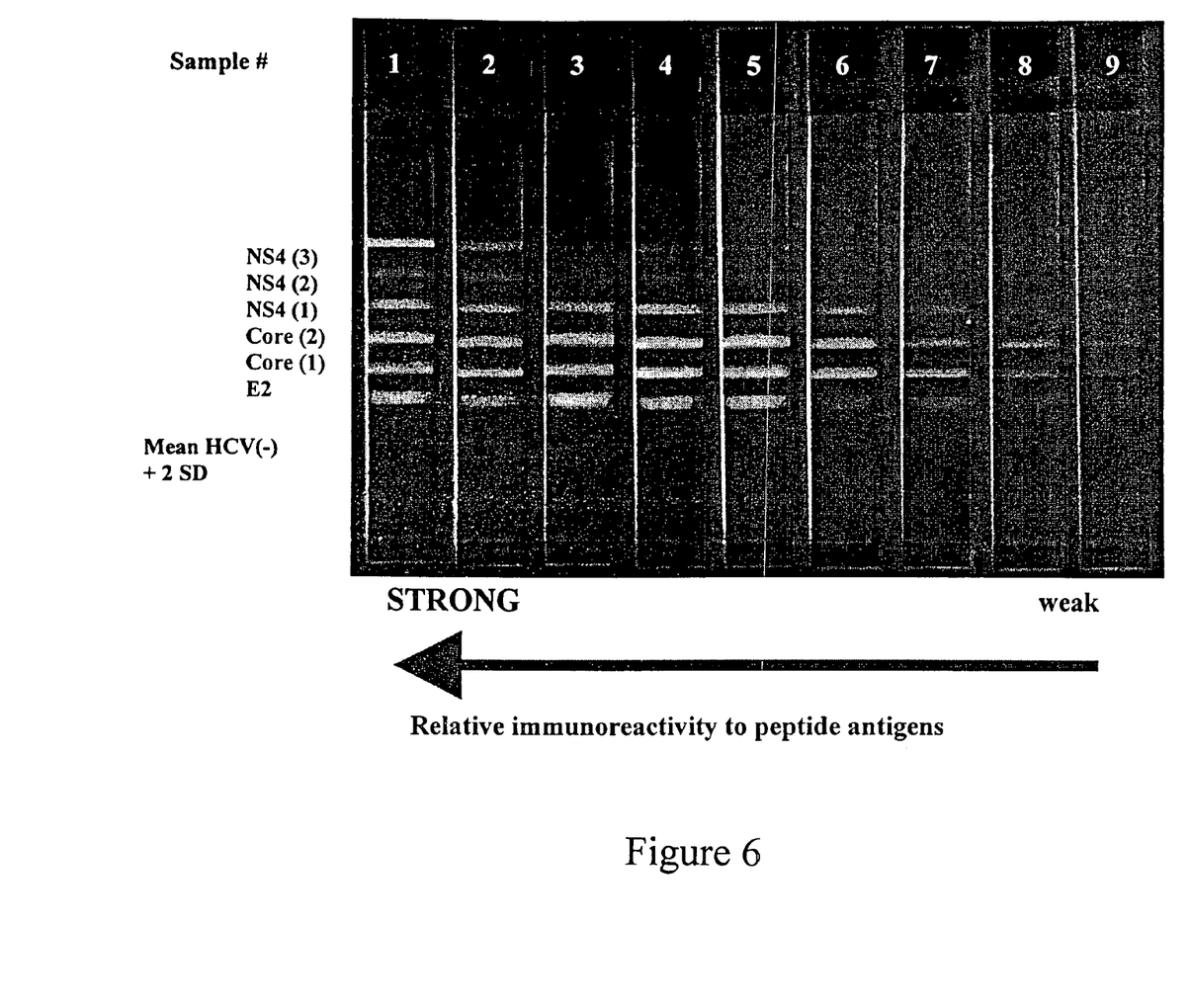
FIG. 6. Antibody profile of 9 individual patient samples using a six-line peptide trapping zone. Patient samples were passed through six different antigen trapping zones to observe the immune response profile for these subjects. Strong responders had high levels of antibody binding against most of the six peptides while weak responders had lower levels of binding within the six trapping zones.

Results of this study clearly show that the antibody response of individual patients can be dissected using this method. This provides a useful means by which antigens to specific genotypes of the HCV virus can be coated onto a suitable matrix and patient samples can then be screened in order to provide information regarding the pattern of antibody response or the strain of virus present (FIG. 5). Such information is useful in tailoring therapy for individual patients on the basis of the HCV genotype present.

The invention has been described with reference to the preferred embodiments. Obviously, modifications and alterations will occur to others upon reading and understanding the preceding detailed description. It is intended that the invention be construed as including all such modifications and alterations in so far as they come within he scope of the appended claims or the equivalents thereof.

We claim:

1. A method for screening for HCV exposure in humans that utilizes an immunoassay for detection of molecule(s) capable of recognizing multiple classes of anti-HCV molecules simultaneously in oral fluid samples comprising the following steps:
   (a) obtaining a sample of oral fluid from a human patient;
   (b) introduction of a labelled anti-human IgG+IgM+IgA antibody cocktail to label IgG, IgM, and IgA antibodies present in the oral fluid sample;
   (c) introduction of the labeled fluid into a flow through affinity matrix having a trapping zone comprised of immobilized HCV peptide antigens;
   (d) selectively capturing labeled antibodies which are specific for the HCV peptide antigens present within the trapping zone of the flow through affinity matrix;
   (e) measuring the binding reaction between the human antibodies and the HCV peptide antigens within the trapping zone by amplified enzymatic reaction, thereby detecting the presence of or the level of IgG, IgM, and IgA antibodies present in the oral fluid sample, wherein the presence of IgG, IgM, and IgA antibodies in the oral fluid sample is indicative of HCV exposure in humans to HCV virus.

2. A method according to claim 1 that utilizes the generation or absence of light, and a light-gathering device to measure said light, to recognize antibody quantity and distribution within the trapping zone.

3. The method according to claim 1 wherein the fluid sample is undiluted saliva.

4. The method according to claim 1 wherein the labeling molecule is AP(alkaline-phosphatase)-conjugated goat anti-human IgG+IgM+IgA antibody cocktail.

5. The method according to claim 1 wherein the screening is completed in 15 minutes or less.

6. The method according to claim 1, wherein the method achieves 98.4% or higher sensitivity at a specificity of 100% for a diagnosis of HCV exposure.

7. The method according to claim 1 wherein the time between obtaining the sample of oral fluid and detecting the level of IgG, IgM, and IgA antibodies present in the oral fluid sample is 15 minutes or less.

8. A method for screening for HCV exposure in humans that utilizes an assay for detection of molecule(s) capable of recognizing multiple classes of anti-HCV molecules simultaneously in oral fluid samples comprising the following steps:
   (a) obtaining a sample of oral fluid from a human patient;
   (f) introduction of a labeling molecule to label IgG, IgM, and IgA antibodies present in the oral fluid sample;
   (g) introduction of the labeled fluid into a flow through affinity matrix having a trapping zone comprised of immobilized HCV peptide antigens;
   (h) selectively capturing labeled antibodies which are specific for the HCV peptide antigens present within the trapping zone of the flow through affinity matrix;
   (i) measuring the binding reaction between the human antibodies and the HCV peptide antigens within the trapping zone by amplified enzymatic reaction, thereby detecting the presence of or the level of IgG, IgM, and IgA antibodies present in the oral fluid sample, wherein the presence of IgG, IgM, and IgA antibodies in the oral fluid sample is indicative of human exposure to HCV.

9. A method according to claim 8, wherein the labeling molecule is a non-antibody molecule used to tag IgG, IgM, and IgA antibodies with a reporter molecule for subsequent detection.

10. The method according to claim 9, wherein the non-antibody molecule is Protein LA.

* * * * *